United States Patent
Otsubo

(10) Patent No.: US 8,168,034 B2
(45) Date of Patent: May 1, 2012

(54) MANUFACTURING METHOD OF ABSORBENT ARTICLE

(75) Inventor: Toshifumi Otsubo, Kanonji (JP)

(73) Assignee: Uni-Charm Corporation, Ehime (JP)

( * ) Notice: Subject to any disclaimer, the term of this patent is extended or adjusted under 35 U.S.C. 154(b) by 149 days.

(21) Appl. No.: 12/389,940

(22) Filed: Feb. 20, 2009

(65) Prior Publication Data

US 2010/0078120 A1 Apr. 1, 2010

(30) Foreign Application Priority Data

Sep. 30, 2008 (JP) ................................. 2008-255190

(51) Int. Cl.
*B32B 37/14* (2006.01)
(52) U.S. Cl. ........ 156/299; 156/179; 156/161; 156/164; 156/176; 156/229; 156/264; 156/301
(58) Field of Classification Search .................. 156/161, 156/164, 176, 229, 264, 301, 299, 179
See application file for complete search history.

(56) References Cited

U.S. PATENT DOCUMENTS

| | | | | |
|---|---|---|---|---|
| 4,657,802 | A | * | 4/1987 | Morman ........................ 428/152 |
| 4,916,005 | A | * | 4/1990 | Lippert et al. ................. 428/192 |
| 2002/0019616 | A1 | * | 2/2002 | Thomas ........................ 604/373 |
| 2002/0136916 | A1 | * | 9/2002 | Cheung et al. ................. 428/517 |
| 2003/0162458 | A1 | * | 8/2003 | Tsujiyama et al. ........... 442/329 |
| 2005/0051276 | A1 | * | 3/2005 | Close et al. .................... 156/498 |
| 2007/0259163 | A1 | * | 11/2007 | Connolly et al. ............. 428/219 |

FOREIGN PATENT DOCUMENTS

| | | |
|---|---|---|
| JP | 06-070958 A | 3/1994 |
| JP | 2001-261207 A | 9/2001 |

* cited by examiner

*Primary Examiner* — Khanh P Nguyen
*Assistant Examiner* — Keith Aziz
(74) *Attorney, Agent, or Firm* — Lowe, Hauptman, Ham & Berner, LLP

(57) ABSTRACT

A manufacturing method of an absorbent article according to the present invention includes the steps of: splitting an elastic member bundle having line-splitting strength within the predetermined range into multiple first elastic members by feeding the elastic member bundle in an MD via a line splitter, the line-splitting strength measured by a predetermined measuring method; applying an adhesive at least on a predetermined curved line on a web continuously conveyed; and placing the multiple elastic members thus split on the web while swinging the elastic members in a CD. The elastic member bundle is formed by splitting a single original elastic member with a slit into the multiple elastic members, and bundling and pressurizing the multiple elastic members.

4 Claims, 5 Drawing Sheets

MANUFACTURING METHOD OF ABSORBENT ARTICLE

RELATED APPLICATIONS

The present application is based on, and claims priority from, Japanese Application Number 2008-255190, filed Sep. 30, 2008, the disclosure of which is hereby incorporated by reference herein in its entirety.

BACKGROUND OF THE INVENTION

1. Field of the Invention

The present invention relates to a manufacturing method of an absorbent article in which multiple elastic members are arranged on a predetermined curved line.

2. Description of the Related Art

Conventionally, a manufacturing method of an absorbent article including the following steps has been known.

Firstly, an elastic member bundle is fed in a conveyance direction (Machine Direction (MD)) via a line splitter, and is thereby split into multiple elastic members.

Secondly, an adhesive is applied at least on a predetermined curved line on a web continuously conveyed.

Thirdly, the multiple elastic members thus split are placed on the web while being swung in a direction (Crossing Direction (CD)) which crosses the conveyance direction.

With the steps, the multiple elastic members can be arranged on the predetermined curved line in a crotch region of the absorbent article.

Here, the elastic member bundle formed by splitting a single original elastic member into multiple elastic members with a slit, and bundling and pressurizing the multiple elastic members is used as the above-described elastic member bundle (for example, see Japanese Patent Application Publication No. H 6-70958 and Japanese Patent No. 3679966).

However, the conventional manufacturing method of an absorbent article has not specifically defined any specification for the elastic member bundle used in the above-described steps, except quality of material and dimensions of each elastic member.

In the above-described steps, since it is required to swing the split multiple elastic members in the CD, a torsion stress acts on an elastic member bundle before being split at a line splitter. This has caused a problem that the elastic member bundle cannot be split into the multiple elastic members properly and the elastic member bundle can be broken easily.

Further, suppose that an autohesive raw material, such as crude rubber, is used as a material (elastic member) to be arranged in the crotch region of the absorbent article. In this case, since it is difficult to make rolls from the material, the material is fed from inside a box in which the material is housed by dropping it down the box. Here, when the material is dropped down into the box thread by thread, the threads can easily tangle with each other in the box since each thread is too thin (about 1 to 2 mm). This tangle can lead to a problem that the thread might be broken during feeding.

As a result, a manufacturing line has to be stopped for installing a new elastic member bundle again, thus resulting in a problem of causing a decrease in production reliability and yield.

Therefore, the present invention has been made in view of the above-described problems, and an object thereof is to provide a manufacturing method of an absorbent article capable of solving the problem that an elastic member bundle can be broken easily at a line splitter, by using an elastic member bundle having line-splitting strength measured by a predetermined measuring method within a predetermined range.

SUMMARY OF THE INVENTION

A first aspect of the present invention provides a manufacturing method of an absorbent article in which multiple elastic members are arranged on a predetermined curved line. The manufacturing method includes the steps of: splitting an elastic member bundle having line-splitting strength within a predetermined range into the multiple elastic members by feeding the elastic member bundle in a conveyance direction via a line splitter, the line-splitting strength measured by a predetermined measuring method; applying an adhesive at least on the predetermined curved line on a web continuously conveyed; and placing the multiple elastic members thus split on the web while swinging the elastic members in a direction which crosses the conveyance direction. In the manufacturing method, the elastic member bundle is formed by splitting a single original elastic member into the multiple elastic members with a slit, and bundling pressurizing the multiple elastic members, and the line-splitting strength of the elastic member bundle indicates a force required to split the multiple elastic members which constitute the elastic member bundle.

As described above, according to the present invention, it is possible to provide the manufacturing method of an absorbent article capable or solving the problem that an elastic member bundle can be broken easily at a line splitter, by using an elastic member bundle having line-splitting strength measured by a predetermined measuring method within a predetermined range.

DESCRIPTION OF THE PREFERRED EMBODIMENT (Manufacturing Method of Absorbent Article According to First Embodiment of Present Invention)

A manufacturing method of an absorbent article according to a first embodiment of the present invention will be described with reference to FIGS. 1 to 5.

Figure 1:
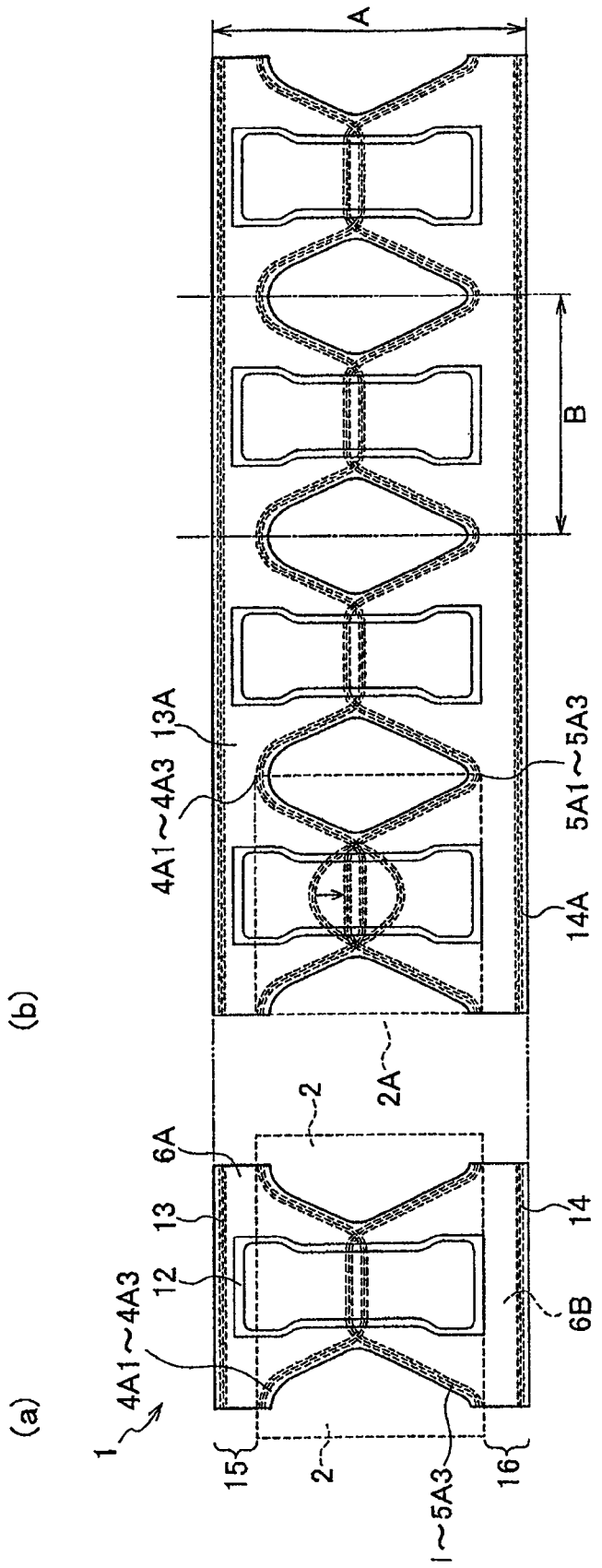
FIG. 1 is a developed plan view of an absorbent article manufactured by a manufacturing method according to a first embodiment of the present invention, and a developed plan view of the absorbent article during manufacturing by the manufacturing method according to the first embodiment of the present invention.

FIG. 1(*a*) is a developed plan view of an absorbent article 1 manufactured by using the manufacturing method according to this embodiment, and FIG. 1(*b*) is a developed plan view of the absorbent article 1 during manufacturing by using the manufacturing method according to this embodiment.

Note that, the absorbent article 1 manufactured by the manufacturing method according to this embodiment may be a pants-type disposable diaper, and may be an open-type disposable diaper.

As shown in FIG. 1(*a*), the absorbent article 1 is provided with a liquid-permeable top sheet 6A, a liquid-impermeable back sheet 6B, an absorbent 12 arranged between the top sheet 6A and the back sheet 63.

Further, the absorbent article 1 includes a front waistband region 15, a rear waistband region 16, and a crotch region 2 located between the front waistband region 15 and the rear waistband region 16.

Here, in the absorbent article 1, multiple first elastic members 4A1 to 4A3 and multiple second elastic members 5A1 to 5A3 are arranged on predetermined curved lines in the crotch region 2.

Note that, this embodiment is configured to arrange three pieces of the first elastic members 4A1 to 4A3 and three pieces of the second elastic members 5A1 to 5A3. However, the numbers of the first elastic member and the second elastic member are not limited to three, but any number can be used.

The first elastic members 4A1 to 4A3 and the second elastic members 5A1 to 5A3 form a leg gather. The leg gather is provided along opening parts for legs.

Note that, the absorbent article 1 may be configured to arrange any one of the first elastic members 4A1 to 4A3 and the second elastic members 5A1 to 5A3 in the crotch region 2.

In the absorbent article 1, one or multiple third elastic members 13 are arranged in the front waistband region 15, and one or multiple fourth elastic members 14 are arranged in the rear waistband region 16. The third elastic members 13 and the fourth elastic members 14 form a waist gather.

Figure 2:
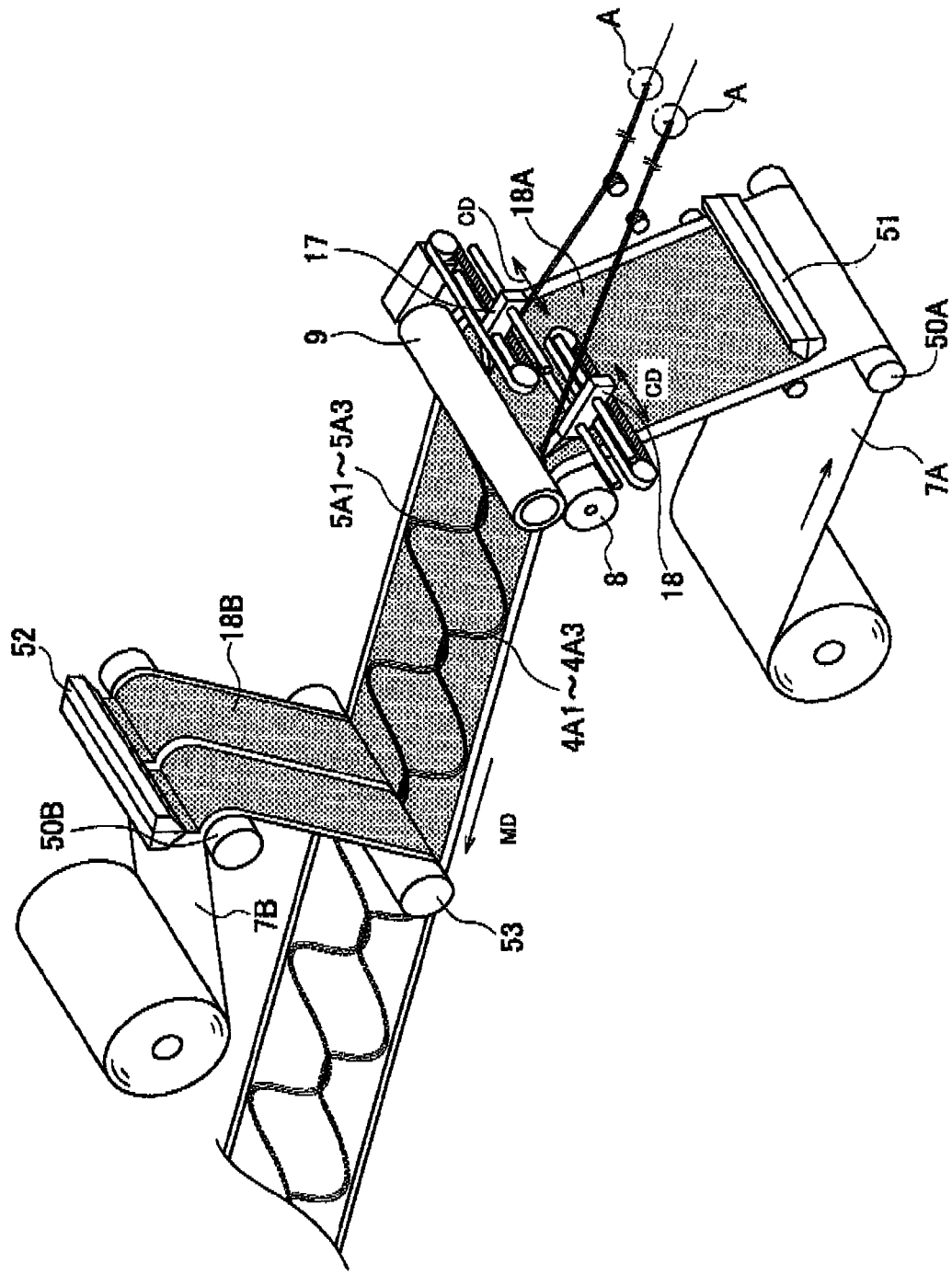
FIG. 2 is a view for explaining the manufacturing method according to the first embodiment of the present invention.
Figure 3:
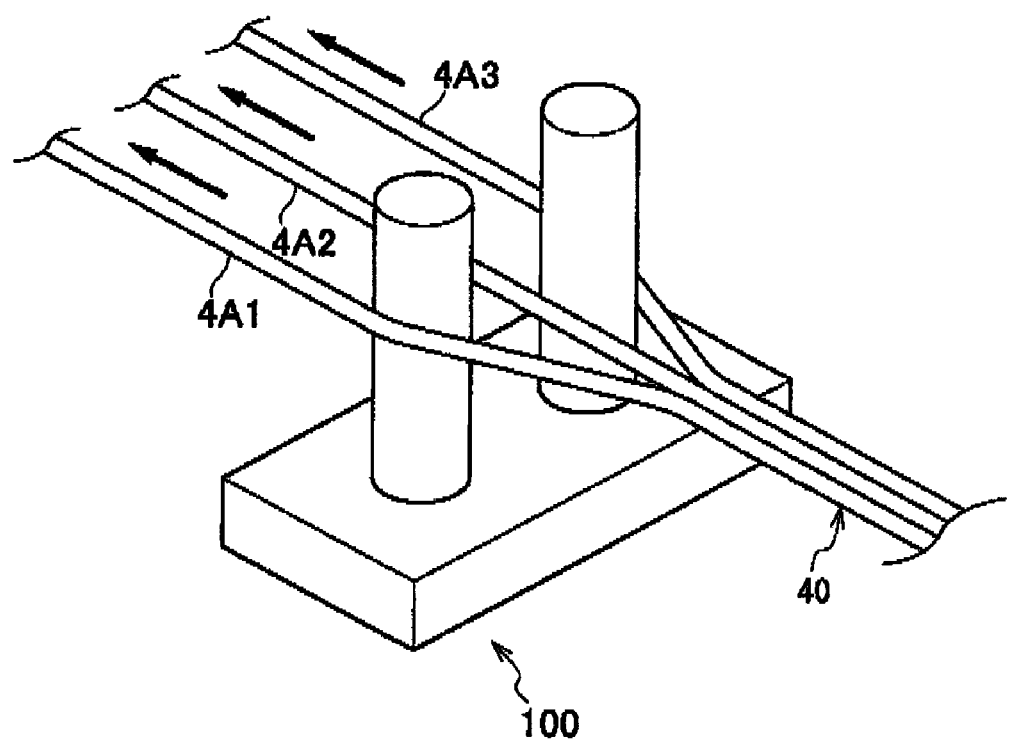
FIG. 3 is a view for explaining a manner of splitting an elastic member bundle into multiple elastic members in the manufacturing method according to the first embodiment of the present invention (enlarged view of a portion A of FIG. 2).

Hereinafter, a step of forming the leg gather in the manufacturing method according to this embodiment will be described with reference to FIGS. 2 and 3. Note that, in the manufacturing method, a width direction (CD) of a first web 7A continuously conveyed corresponds to a longitudinal direction of the absorbent article 1, and a longitudinal direction (MD) of the first web 7A corresponds to a width direction of the absorbent article 1.

Firstly, elastic member bundles 40, 50 having a line-splitting strength, which is measured by a predetermined measuring method (to be described later), within a predetermined range are fed in the MD via a line splitter 100 formed of a metal stick or the like, thereby splitting the elastic member bundles 40, 50 into the multiple first elastic members 4A1 to 4A3 and the second elastic members 5A1 to 5A3.

The elastic member bundle 40 (or 50) is formed in such a manner that a single original elastic member is split with a slit into the multiple elastic members 4A1 to 4A3 (or 5A1 to 5A3), and the multiple elastic members 4A1 to 4A3 (or 5A1 to 5A3) are bundled and pressurized.

For example, as such an original elastic member, a material which is composed of crude rubber, synthetic rubber, or the like and whose cross section has a substantially circular or a rectangular shape is used. Further, the cross section of each of the elastic members 4A1 to 4A3 (or 5A1 to 5A3) has a substantially circular or a rectangular shape.

Particularly, in a case where the cross section of each of the elastic members 4A1 to 4A3 (or 5A1 to 5A3) has a rectangular shape, a change of stress between before and after the elastic members pass through the line splitter 100 is larger than a case where the cross section of each of the elastic members 4A1 to 4A3 (or 5A1 to 5A3) has a substantially circular shape, so that a tearing force in the line splitter 100 is not stabilized. Therefore, in the case where the cross section of each of the elastic members 4A1 to 4A3 (or 5A1 to 5A3) has a rectangular shape, the effect of the manufacturing method of an absorbent article of the present invention exhibits its remarkably.

Secondly, the first web 7A is paid out from a first web whole material, and a traveling direction of the first web 7A is turned by a guide roll 50A.

Thirdly, an adhesive applying device 51 applies an adhesive 18A on a predetermined position, on an opposite surface to a second web 7B, of the first web 7A (at least on a predetermined curved line).

Fourthly, the first elastic members 4A1 to 4A3 and the second elastic members 5A1 to 5A3 are placed on the predetermined curved line on at least one surface of the first web 7A on which the adhesive 18A is applied, while being swung by a first swing guide 18 and a second swing guide 17, respectively, in a CD (a direction crossing the conveyance direction) of the first web 7A.

Here, the predetermined curved line on which the first elastic members 4A1 to 4A3 are placed may differ from the predetermined curved line on which the second elastic members 5A1 to 5A3 are placed.

Fifthly, the first web 7A on which the first elastic members 4A1 to 4A3 and the second elastic members 5A1 to 5A3 are placed is fed between a first roll 8 and a second roll 9 which rotate in the MD so that the first elastic members 4A1 to 4A3, the second elastic members 5A1 to 5A3, and the first web 7A can be pinched and pressed.

Sixthly, an adhesive applying device 52 applies an adhesive 18B on a predetermined position, on an opposite surface to the first web 7A, of the second web 7B which is paid out from a second web whole material (at least on a predetermined curved line).

Seventhly, a roll 53 bonds a surface of the first web 7A on which the first elastic members 4A1 to 4A3 and the second elastic members 5A1 to 5A3 are bonded, and a surface of the second web 7B on which the adhesive 18B is applied.

In this manner, the first elastic members 4A1 to 4A3 and the second elastic members 5A1 to 5A3 which constitute the leg gather can be arranged between the first web 4A and the second web 5A.

Hereinafter, a method of measuring the line-splitting strength of the elastic member bundles 40, 50 used in the manufacturing method according to this embodiment will be described. Here, the line-splitting strength of the elastic member bundle 40 (or 50) indicates a force required to split the multiple elastic members 4A1 to 4A3 (or 5A1 to 5A3) which constitute the elastic member bundle 40 (or 50). As a unit of the line-splitting strength, g/piece or N/piece can be used, for example.

Figure 4:
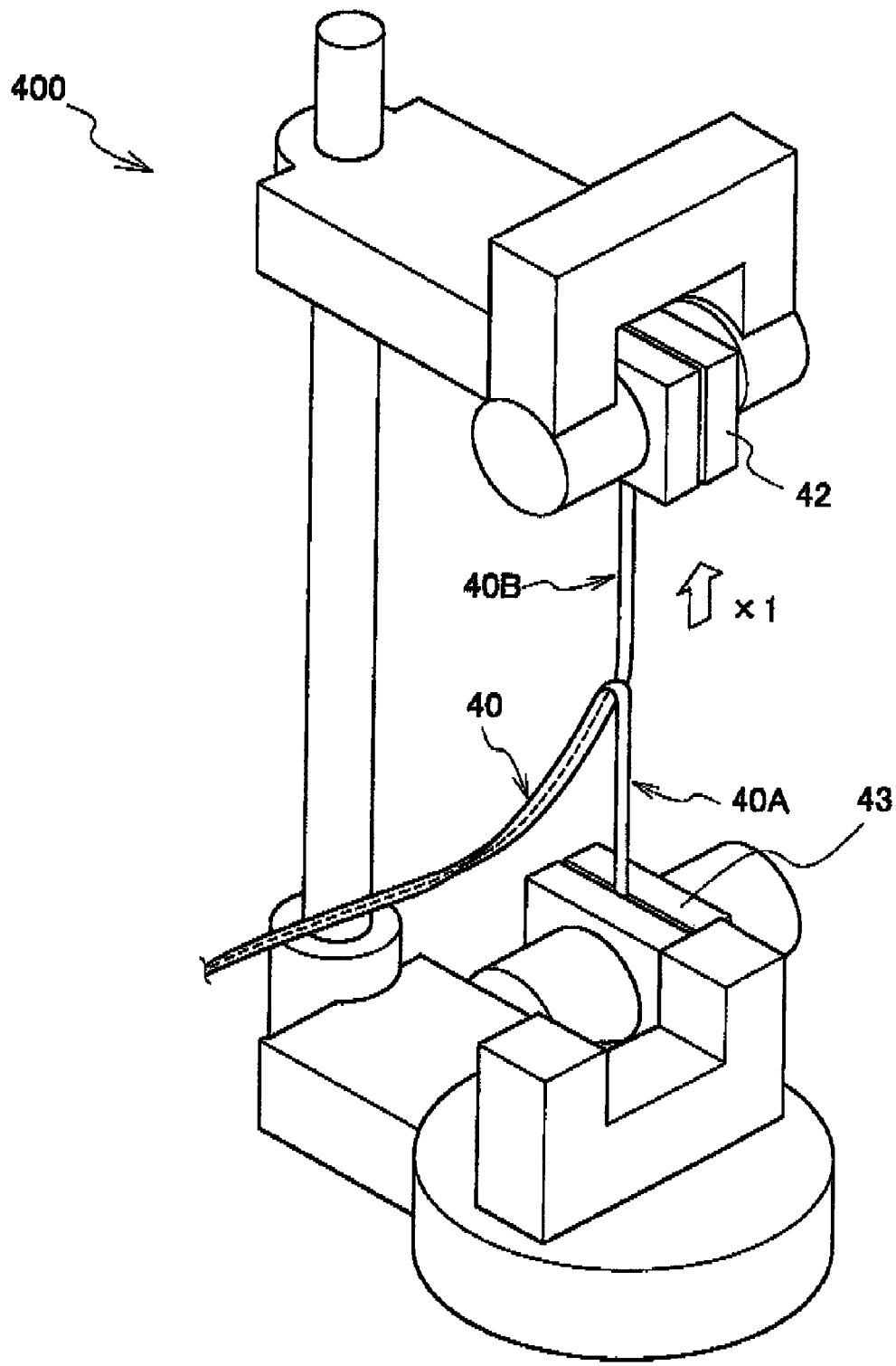
FIG. 4 is a view for explaining an example of a method of measuring line-splitting strength of the elastic member bundle used in the manufacturing method according to the first embodiment of the present invention.

For example, the line-splitting strength of the elastic member bundles 40, 50 can be measured with a measuring method including the following steps (see FIG. 4).

Firstly, in a measurement device 400, a chuck part 43 chucks and fixes an elastic member 40A to be measured, and a chuck part 42 pulls an elastic member bundle 40B not including the elastic member 40A at a predetermined speed X1 while chucking the elastic member bundle 40B. Alternatively, the chuck part 43 chucks and fixes the elastic member bundle 40B not including the elastic member 40A, and the chuck part 42 pulls the elastic member 40A to be measured at the predetermined speed X1 while chucking the elastic member 40A.

Secondly, a maximum load applied when the elastic member 40A to be measured is split is determined as the above-described line-splitting strength.

In this measuring method, when a length of each elastic member bundle is set to 300 mm; when the predetermined speed X1 is set to 200 mm/second; when chucked lengths of the elastic member 40A and the elastic member bundle 40B by the chuck parts 42, 43 in the measurement device 400 are set to 25 mm; and when a distance between the chuck parts 42, 43 of the measurement device 400 is set to 50 mm, it is preferable to use the elastic member bundles 40, 50 having the line-splitting strength measured by this measuring method within a range of 25 mN/piece or less in the above-described manufacturing method. Note that, the elastic member bundles 40, 50 need to be bundled with a strength not to be automatically split during the conveyance.

Here, it is assumed that the elastic member bundles 40, 50 are used in the above-described manufacturing method in which a conveyance speed of each of the elastic member bundles 40, 50 is set to 100 m/minute; a draw ratio thereof is set to 1.3 to 3 times; and a maximum angle between a tangent line of the arranged elastic members 4A1 to 4A3 (or, 5A1 to 5A3) and the center line in the MD thereof is set to 68 degrees.

Figure 5:
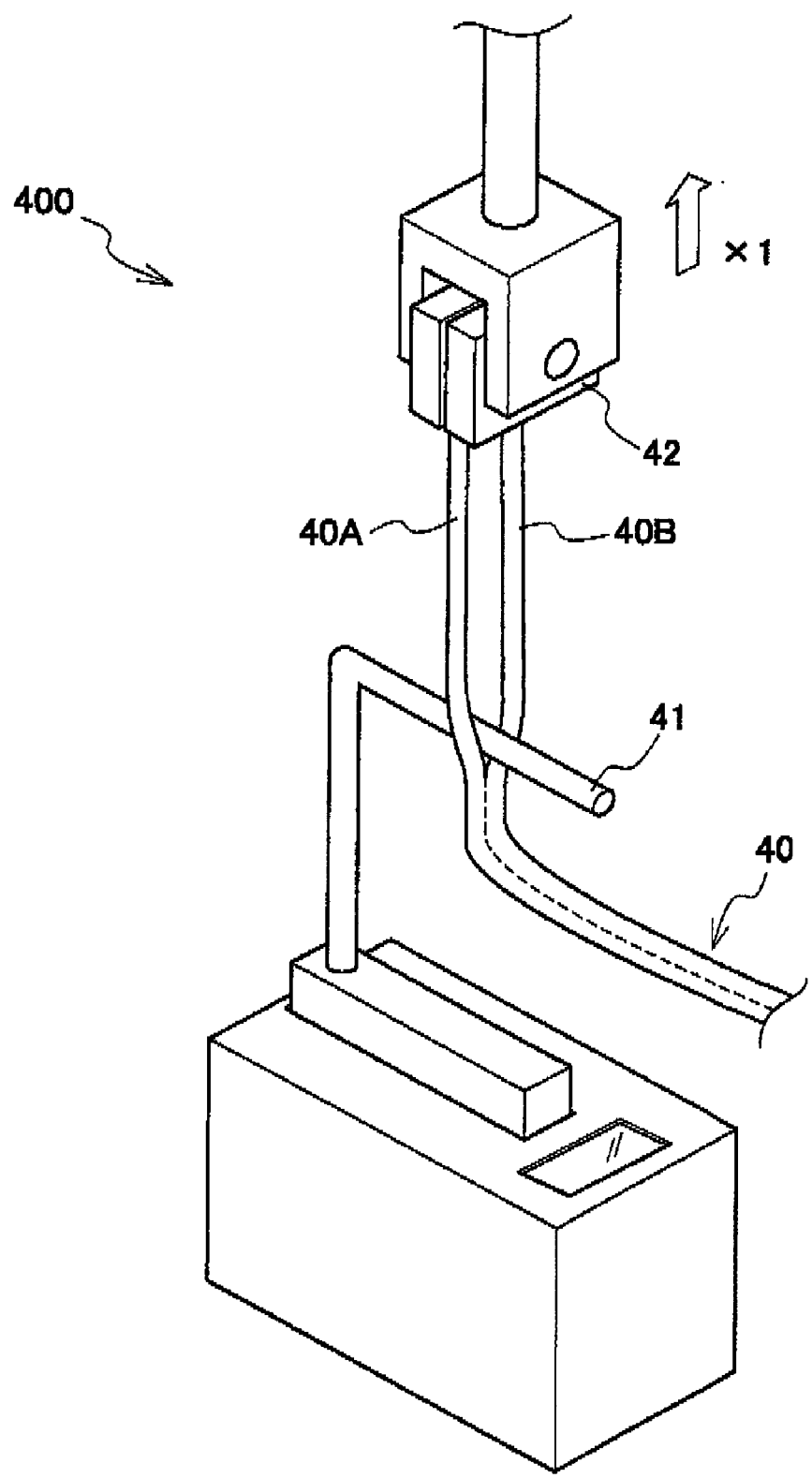
FIG. 5 is a view for explaining another example of a method of measuring the line-splitting strength of the elastic member bundle used in the manufacturing method according to the first embodiment of the present invention.

Further, the line-splitting strength of the elastic member bundles 40, 50 can be measured with a measuring method including the following steps (see FIG. 5).

Firstly, in a state where a hook 41 is set between the elastic member 40A to be measured and the remaining elastic member bundle 40B in the measurement device 400, the chuck part 42 pulls one end of the elastic member 40A to be measured and one end of the remaining elastic member bundle 40B at the predetermined speed X1 while chucking one ends thereof.

Secondly, the maximum load applied when the elastic member 40A to be measured is split is determined as the above-described line-splitting strength.

In this measuring method, when the length of each elastic member bundle is set to 300 mm; when the predetermined speed X1 is set to 100 mm/second; when the chucked lengths of the elastic member 40A and the elastic member bundle 40B by the chuck part 42 in the measurement device 400 are set to 25 mm; and when the distance between the chuck part 42 and the hook 41 of the measurement device 400 is set to 50 mm, it is preferable to use the elastic member bundles 40, 50 each having the line-splitting strength measured by this measuring method within the range of 25 mN/piece or less, in the above-described manufacturing method. Note that, the elastic member bundles 40, 50 need to be bundled with a strength not to be automatically split during the conveyance.

Here, it is assumed that the elastic member bundles 40, 50 are used in the above-described manufacturing method in which the conveyance speed of the elastic member bundles 40, 50 is set to 100 m/minute, the draw ratio thereof is set to 1.3 to 3 times, and the maximum angle between the tangent line of the arranged elastic members 4A1 to 4A3 (or, 5A1 to 5A3) and the center line in the MD thereof is set to 68 degrees.

Note that, a pressure to be applied when the multiple elastic members 4A1 to 4A3 (or 5A1 to 5A3) are bundled at the time of forming the elastic member bundles 40, 50, is determined in consideration of quality of material of the original elastic member, a thickness (a diameter, a width, and the like) of the elastic member, and the like.

According to the manufacturing method according to the first embodiment of the present invention, the elastic member bundle 40 having the line-splitting strength within the predetermined range is only used as the elastic member bundle 40 used for forming the leg gather. Thus, it is possible to reduce a defect that the elastic member bundle 40 is broken when being fed in the MD via the line splitter 100. This contributes to a stable production and an improvement in yield.

As described above, the present invention has been described in detail by using the above-described embodiment. However, it is apparent to those skilled in the art that the present invention is not limited to the embodiment described in this description. The present invention can be modified and changed without departing from the gist and the scope of the present invention defined by the appended claims. Therefore, the description is aimed at illustration and explanation of the present invention, and does not have any meaning which limits the present invention.

What is claimed is:

1. A method of manufacturing an absorbent article in which a plurality of elastic members are arranged on a predetermined curved line, the method comprising the steps of:
    splitting an elastic member bundle, which has a line-splitting strength within a predetermined range into the plurality of elastic members by feeding the elastic member bundle in a conveyance direction via a line splitter, the line-splitting strength being measured by a predetermined measuring method;
    applying an adhesive at least on the predetermined curved line on a web continuously conveyed in the conveyance direction; and
    placing the plurality of elastic members thus split on the web while swinging the elastic members in a direction which crosses the conveyance direction,
    wherein
    the elastic member bundle is formed by splitting a single original elastic member with slits into the plurality of elastic members, and bundling and pressurizing the plurality of elastic members into said elastic member bundle in which said elastic members are bundled together, in direct contact with each other, and splittable with the line-splitting strength which is no more than 25 mN/piece,
    the line-splitting strength of the elastic member bundle indicates a force required to individually split the plurality of elastic members from the elastic member bundle.

2. The method according to claim 1, wherein
    the absorbent article is a disposable diaper including a front waistband region, a rear waistband region, and a crotch region located between the front waistband region and the rear waistband region, and
    the plurality of elastic members are arranged in the crotch region.

3. The method according to claim 1, wherein the measuring method includes the steps of:
    pulling one of (i) the elastic member of the elastic member bundle to be measured and (ii) the remaining elastic members of the elastic member bundle at a predetermined speed while fixing the other; and
    determining a maximum load applied when the elastic member is split from the elastic member bundle as the line-splitting strength.

4. The method according to claim 1, wherein the measuring method includes the steps of
    pulling one end of one elastic member in the elastic member bundle to be measured and one end of the remaining elastic members of the elastic member bundle at a predetermined speed while setting a hook between said elastic member and the remaining elastic members of the elastic member bundle; and
    determining a maximum load applied when the elastic member is split from the elastic member bundle as the line-splitting strength.

* * * * *